United States Patent [19]
Shinzato

[11] Patent Number: 5,370,123
[45] Date of Patent: Dec. 6, 1994

[54] BLOOD CLARIFICATION APPARATUS

[75] Inventor: Toru Shinzato, Asai Haitsu 202, 2-506, Inokoishi, Meito-ku, Nagoya-shi, Aichi-ken, Japan

[73] Assignees: Nissho Corporation, Osaka; Toru Shinzato, Nagoya, both of Japan

[21] Appl. No.: 147,445

[22] Filed: Nov. 5, 1993

Related U.S. Application Data

[63] Continuation of Ser. No. 829,356, Feb. 3, 1992, abandoned.

[30] Foreign Application Priority Data

Apr. 4, 1991 [JP] Japan .................... 3-035600

[51] Int. Cl.$^5$ ............................................. A61B 5/00
[52] U.S. Cl. ................................. 128/673; 604/4
[58] Field of Search ............... 128/673; 604/4–6, 604/29–31, 64–66

[56] References Cited

U.S. PATENT DOCUMENTS

| | | | |
|---|---|---|---|
| 4,098,274 | 7/1978 | Ebling et al. | 128/673 |
| 4,466,804 | 8/1984 | Hino | 604/31 |
| 4,501,583 | 2/1985 | Troutner . | |
| 4,648,406 | 3/1987 | Miller | 128/674 |
| 4,718,890 | 1/1988 | Peabody | 604/65 |
| 4,718,891 | 1/1988 | Lipps | 604/67 |
| 4,813,423 | 3/1989 | Miyasaka et al. | 128/673 |
| 4,846,191 | 7/1989 | Brockway et al. | 128/673 |
| 4,928,693 | 5/1990 | Goodin et al. . | |
| 4,944,724 | 7/1990 | Goldberg | 128/673 |

FOREIGN PATENT DOCUMENTS 2179980  11/1973  France .
60-12073  1/1985  Japan .

OTHER PUBLICATIONS

Patent Abstracts of Japan, vol. 13, No. 95, Mar. 6, 1989.

*Primary Examiner*—Lee S. Cohen
*Assistant Examiner*—Robert L. Nasser
*Attorney, Agent, or Firm*—Armstrong, Westerman, Hattori, McLeland & Naughton

[57] ABSTRACT

A blood clarification device wherein a means for measuring blood pressure comprises (a) a needle-detector which is much thinner than the puncture needle and capable of being smoothly inserted into a blood vessel from outside through an inner aperture of the puncture needle, (b) an insertion aperture, for allowing fluid-tight insertion of the needle-detector, positioned on a wall of the blood supply passage in the vicinity of the puncture needle, and (c) a pressure transducer for detecting the blood pressure inside the blood vessel transmitted thereto via the needle-detector. In a blood clarification apparatus of the present invention, blood pressure inside a blood vessel is transmitted to a pressure transducer via a needle-detector during dialysis/filtration operation and blood pressure of a patient is detected continuously and automatically by the pressure transducer. A counterplan such as control of water-removing-rate or supplying-supplementary-fluid-rate based on the detected blood pressure is automatically carried out, so that safety of dialysis/filtration operation can be effectively improved.

1 Claim, 4 Drawing Sheets

BLOOD CLARIFICATION APPARATUS

This application is a continuation of application Ser. No. 07/829,356, filed Feb. 3, 1992, now abandoned.

BACKGROUND OF THE INVENTION

The present invention generally relates to a blood clarification apparatus. More particularly, the present invention relates to a blood clarification apparatus, wherein occurrence of hypotension attack can be effectively prevented during dialysis/filtration operation, and safety and operation characteristics can be effectively improved.

Recently, a medical treatment by blood clarification, using a so-called artificial organ, is generally employed and its distinguishing effect is recognized. During treatment, blood once taken out from a living body is circulated through a housing enclosing a semipermeable membrane; the blood is subjected to a predetermined clarifying action by dialyzing or filtering action with the semipermeable membrane; the amount of the blood is controlled by removal of water; and thereafter the blood is brought back into the living body. Thus, renal function and liver function are artificially achieved. For example, a medical treatment by blood dialysis or filtration with the use of a so-called artificial kidney, which is applied to a renal insufficiency patient, is a typical one.

Hereupon, in carrying out blood clarification with an artificial kidney, it is necessary to take out blood from a spot of a living body where enough blood can be obtained. Since enough blood is difficult to be obtained from a vein existing in a vicinity a body surface, a shunt operation is generally performed. The shunt is an operation wherein, for example, at a region such as an arm, one of the arteries existing in a deep area of a body is connected with a vein existing in a vicinity of a body surface to bypass them. By this method, an amount of blood running through a vein can be increased. Then, a thick needle (a puncture needle) generally of 15 to 17 gage is used to puncture the fistula (namely, the arteried vein); and blood is taken out at a rate of about 250 ml/min by using a blood pump to lead the blood to a clarification device. In this device, clarification and removal of water in the blood are carried out.

Due to the above-mentioned treatment, a phenomenon sometimes occurs wherein blood pressure is abnormally lowered during the dialyzing, in a certain patient undergoing medical treatment by the blood dialyzing (the word "dialyzing" used hereinafter includes filtration). This sharp lowering of blood pressure causes symptoms of vomiting and cramp, and loss of awareness. In an extreme case, the lowering of blood pressure may endanger the life of a patient. This is a so-called dialysis hypotension. It is recognized that 10 to 20% of all patients received shock two or three times in one medical treatment by blood dialyzing.

In order to prevent the occurrence of dialysis hypotension symptoms during the dialysis operation, it is necessary to measure blood pressure of the patient continuously and to consider counterplans such as control of water-removing-rate and/or supply of supplementary fluid into blood based on the change of blood pressure.

However, since conventional dialysis apparatus does not have a suitable means for automatically measuring blood pressure, it is necessary for a nurse or such person to measure blood pressure at a predetermined time interval by usual auscultation, and to manually control the water-removing-rate or supply supplementary fluid. The operation takes a great deal of trouble for the patients and operators. Moreover, since the dialysis hypotension occurs at intervals of one or two minutes, it is very difficult to immediately find the occurrence of the shock as well as to predict the occurrence of the shock based on the above-mentioned measurement of blood pressure at a predetermined time interval. For this reason, the counterplan for the shock is likely to be late.

Hitherto, in order to measure blood pressure in a blood vessel, a needle has been produced having two apertures parallel to each other wherein one of the apertures is utilized for taking out blood from a blood vessel and the other is utilized for transmitting blood pressure inside the blood vessel to a pressure transducer. However, the needle having two apertures is expensive because of its complicated producing steps. Further, since its outer diameter becomes much thicker than that of conventional puncture needles, the blood stanching is very difficult after taking out the needle. For these reasons, the needle having two apertures has not been used practically.

The present invention was made to solve the above-mentioned drawbacks, and it is thus an object of the present invention to prevent the dialysis hypotension by continuously and automotially measuring blood pressure during dialysis/filtration operation and by enabling the control of water-removing-rate or supply of supplementary fluid based on measurement of blood pressure.

SUMMARY OF THE INVENTION

In accordance with the present invention, there is provided a blood clarification apparatus wherein (1) blood taken out from a blood vessel by a puncture needle is introduced to a blood clarification device via a blood supply passage and is clarified by dialyzing and/or filtering action, and water contained in the blood is removed; and (2) blood pressure inside the blood vessel is continuously measured by a means for measuring blood pressure, and water-removing-rate and/or supplementary-fluid-supplying-rate into a body is controlled based on the measured blood pressure characterized in that the means for measuring blood pressure comprises a needle-shaped pipe for detecting blood pressure, which is much thinner than the puncture needle and capable of being smoothly inserted into a blood vessel from outside through an inner aperture of the puncture needle, an insertion aperture, for allowing fluid-tight insertion of the needle-shaped pipe for detecting blood pressure, on a wall of the blood supply passage in the vicinity of the puncture needle, and a pressure transducer for detecting the blood pressure inside the blood vessel transmitted to the pressure transducer via the needle-shaped pipe for detecting blood pressure.

In a blood clarification apparatus of the present invention, blood pressure inside a blood vessel is transmitted to a pressure transducer via a needle-shaped pipe for detecting blood pressure, which is to be positioned, during dialysis/filtration operation, in a body via an inner aperture of a puncture needle. Blood pressure of a patient is detected continuously and automatically by the pressure transducer, and a counterplan (such as, control of water-removing-rate or supply of supplementary fluid based on the detected blood pressure) is taken so that safety of dialysis/filtration operation can be effectively improved.

Further, in the apparatus of the present invention, a needle-shaped pipe for detecting blood pressure, for detecting blood pressure is inserted through an insertion aperture for needle detector made on a wall of a blood supply passage (normally defined by synthetic resin tube) at downstream of a puncture needle for taking out blood. The needle-shaped pipe for detecting blood pressure, is further brought into a blood vessel through an inner aperture of the puncture needle, so that it is not necessary to directly stick a needle-shaped pipe for detecting blood pressure, into a blood vessel through a skin. For this reason, the apparatus of the present invention does not give pain and discomfort to patients.

It is a characteristic feature of the apparatus of the present invention for air not to be introduced into blood or for blood not to leak out from the insertion position of a needle-shaped pipe for detecting blood pressure, since the insertion aperture has a good sealing characteristic and the outer diameter of the needle-shaped pipe for detecting blood pressure is sufficiently thin. Further, it is a significant characteristic of the apparatus of the present invention for the pointed head of the needle-shaped pipe for detecting blood pressure to always be kept deep enough inside the blood vessel, since the insertion aperture for the needle-shaped pipe for detecting blood pressure is arranged at a suitable position on a wall of a blood supply passage (synthetic resin tube) positioned at a downstream of the puncture needle.

Further, the apparatus of the present invention can be economically produced because the above-mentioned means for measuring blood pressure employs a structural arrangement wherein a needle-shaped pipe for detecting blood pressure of a simple structure is introduced into a blood vessel through an inner aperture of a conventional puncture needle, and blood pressure transmitted via the inner aperture of the puncture needle is measured. Since the needle-shaped pipe for detecting blood pressure having sufficiently thin outer diameter relative to the inner diameter of the puncture needle is employed, there is no danger that the existence of the needle-detector causes large resistance against blood current running through the puncture needle.

DETAILED DESCRIPTION

Next, an embodiment of a blood clarification apparatus of the present invention is explained below in detail with reference to the drawings.

Figure 1:
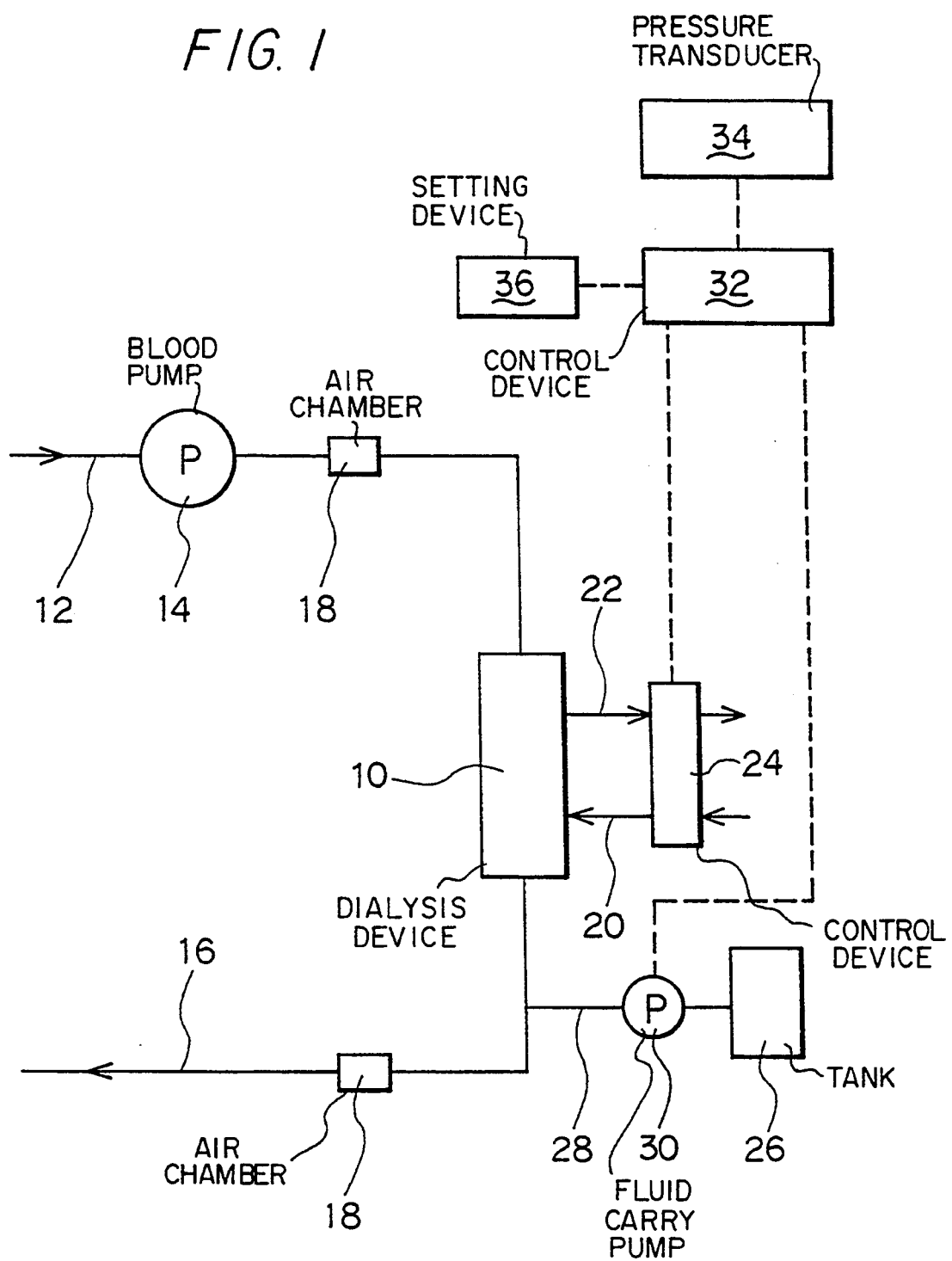
FIG. 1 is a schematic explanatory view of an embodiment of a blood clarification apparatus of the present invention.

FIG. 1 is a schematic view of a blood clarification apparatus of the present invention. In FIG. 1, numeral 10 represents a dialysis device (dialyzer) which includes a housing in which film-like, tube-like or hollow-fiber-like semipermeable membrane is enclosed. The dialysis device 10 is connected with a blood supply passage 12 for introducing blood taken out from a patient body via a puncture needle 42 (refer to FIG. 2 ). A predetermined mount of blood is introduced to the dialysis device 10 by a blood pump 14 positioned at a path of the blood supply passage 12. The blood clarified by the dialysis device 10 is returned to the patient's body through a blood carry passage 16. The blood supply passage 12 and the blood carry passage 16 are respectively equipped with an air chamber 18 so that air is prevented from entering the patient's body.

A dialyzate supply passage 20 and a dialyzate discharge passage 22 are connected with the dialysis device 10. The passage 20 serves to introduce dialyzate to the device 10. The passage 22 serves to discharge dialyzate brought in contact with blood through the semipermeable membrane in the dialysis device 10, or to discharge undesired or harmful substance taken out from the blood by dialyzing and/or filtering action of the semipermeable membrane. At a respective path of the dialyzate supply passage 20 and the dialyzate discharge passage 22, a known control device 24 for dialyzate supply and water removal is arranged. The device 24 controls dialyzate flow rate and dialyzate pressure. By this control device 24, pressure difference between blood side and dialyzate side which are partitioned by the semipermeable membrane in the dialysis device 10 is controlled, and the removal of water from the inside of body is carried out depending on the pressure difference.

A fluid carry passage 28 communicating with a tank 26 for supplementary fluid is connected with the path of the blood carry passage 16. In the tank 26 electrolyte (supplementary fluid) such as physiological salt solution is contained. By a fluid carry pump 30 arranged at a path of the passage 28, the electrolyte is supplemented or supplied to concentrated blood after filtration. The blood, having composition of blood component which is controlled by the above-mentioned operation, is returned to the patient's body through the blood carry passage 16.

In the present embodiment, as shown in FIG. 1, the operation of the control device 24 for dialyzate supply and water removal which controls the amount of water removal by the dialysis device 10 and the operation of the fluid carry pump 30 which controls the amount of supply of supplementary fluid are controlled by a water-removal/supplementary-fluid-supply control device 32. The control device 32 is connected with a pressure transducer 34 which measures blood pressure. The blood pressure value of the patient inputted from the pressure transducer 34 is compared with a reference value predetermined by a setting device 36. Based on the compared value, the device 32 controls the operation of the device 24 and the pump 30.

Figure 2:
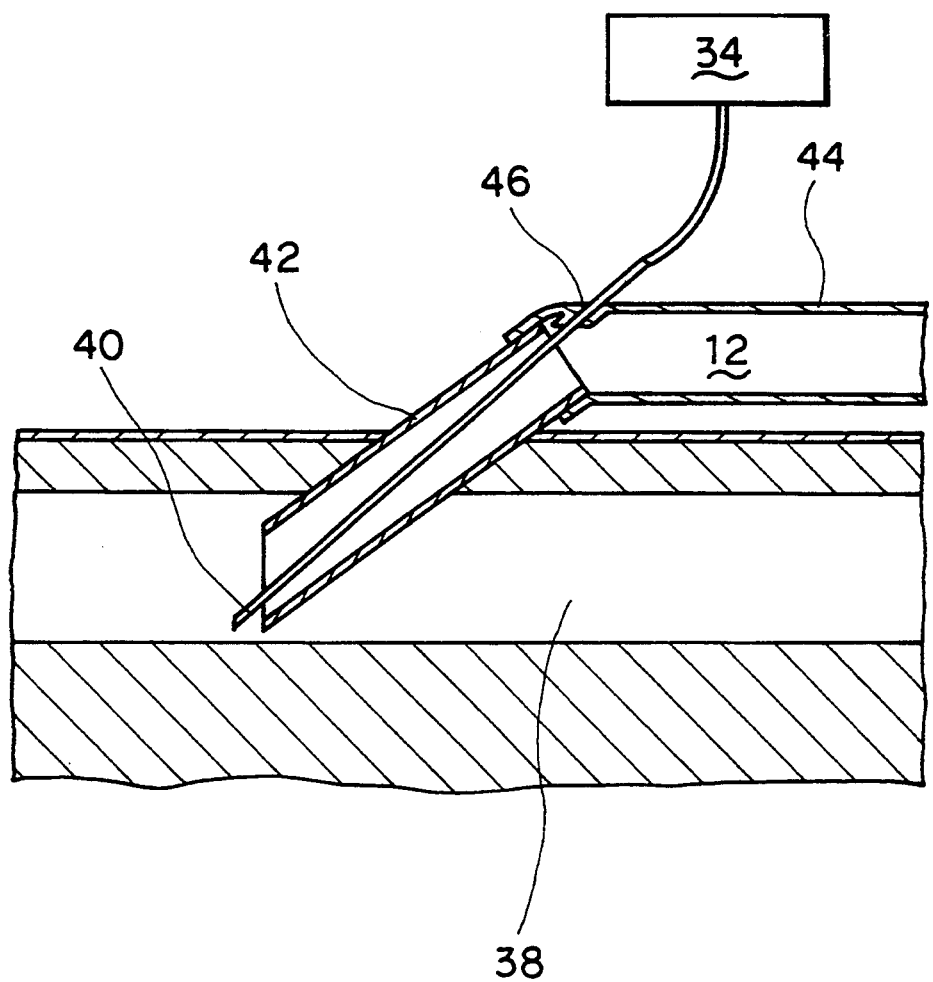
FIG. 2 is an explanatory view showing a means for detecting blood pressure in the apparatus of FIG. 1.

As shown in FIG. 2, a needle-shaped pipe 40 for detecting blood pressure, the pointed head of which is introduced into a blood vessel 38 lying for example in an arm of a patient, is connected with the pressure transducer 34. Thus, blood pressure inside the blood vessel 38 is transmitted to the pressure transducer 34 via the needle-shaped pipe 40 for detecting blood pressure. The inner aperture of the needle-shaped pipe 40 for detecting blood pressure is filled with physiological salt solution so that blood does not enter the needle-shaped pipe 40 for detecting blood pressure. When the needle-shaped pipe 40 for detecting blood pressure is sticked into the blood vessel 38 in an inverse direction to that of blood current, the blood pressure inside the blood vessel 38 is transmitted to the physiological salt solution inside the needle-shaped pipe 40 for detecting blood pressure and is further transmitted to the pressure transducer 34. In this way, the blood pressure inside the blood vessel 38 can be continuously detected by the pressure transducer 34.

The needle-shaped pipe 40 for detecting blood pressure is not directly sticked into the arm of the patient, but is introduced deep enough to reach inside of the blood vessel 38 through an inner aperture of a puncture needle 42 which is sticked into the blood vessel 38 for taking out blood from the body. That is, in the present embodiment, the needle-shaped pipe 40 for detecting blood pressure is inserted into a blood path through an insertion aperture 46 and is led into the blood vessel 38 through the inner aperture of the puncture needle 42. The insertion aperture 46 for the needle-shaped pipe 40 for detecting blood pressure is formed on a wall of a tube 44 made of synthetic resin in the vicinity of the puncture needle 42. The tube 44 is connected with the puncture needle 42 and serves as a blood supply passage 12. In other words, the insertion aperture 46 is formed on the wall at a position apart from a connected area of the puncture needle 42 and the tube 44 by 5 to 10 mm. The insertion aperture 46 is formed with a member having a good sealing characteristic such as rubber valve.

When the needle-shaped pipe 40 for detecting blood pressure is placed as stated above, the patient is not pierced with an additional needle for measuring blood pressure. Further, once the needle-shaped pipe 40 for detecting blood pressure is applied to the patient, attachment or detachment of the needle-shaped pipe 40 for detecting blood pressure is not carried out until the dialysis is finished; thus, the installation of the needle-shaped pipe 40 for detecting blood pressure is not a burden for the patient. Since blood pressure is detected continuously and automatially by the pressure transducer 34 during dialyzing operation by merely respectively attaching and detaching the needle-shaped pipe 40 for detecting blood pressure one time, the burden of monitoring fluctuation of blood pressure can be significantly reduced for a person measuring blood pressure.

The pressure inside the inner aperture of the tube 44 and the puncture needle 42, both of which serve as the blood supply passage 12, becomes low and not more than the atmospheric pressure by the operation of the blood pump 14. For example, when blood is taken out at a rate of 200 ml/min, the inside pressure becomes about $-40$ mmHg. So, if the pointed head of the needle-shaped pipe 40 for detecting blood pressure exists in the puncture needle 42, then also one might think of the possibility that blood pressure transmitted through the needle-shaped pipe 40 for detecting blood pressure becomes much lower than the arterial pressure under the influence of such a negative pressure. However, if the pointed head of the needle-shaped pipe 40 for detecting blood pressure is so placed as to sufficiently project from the pointed head of the puncture needle 42 so that the pointed head of the needle-shaped pipe 40 for detecting blood pressure reaches a deep position in the blood vessel 38, blood pressure in the blood vessel 38 can be measured exactly almost without the influence of the negative pressure.

Considering the above-mentioned condition, in the present embodiment, the insertion aperture 46 is formed on the wall of the synthetic resin tube 44, which is connected with the puncture needle 42, at a suitable distance from the connected area with the puncture needle 42. Therefore, the needle-shaped pipe 40 for detecting blood pressure can be easily inserted from the aperture 46, and the pointed head of the needle-shaped pipe 40 for detecting blood pressure can be kept at a suitable position in the blood vessel 38. Moreover, by employing an insertion aperture having a good sealing characteristic as the insertion aperture 46, air entering the blood or the blood leaking out from the insertion aperture 46 is effectively prevented. Although the puncture needle 42 and the needle-shaped pipe 40 for detecting blood pressure are generally applied to a shunted blood vessel, the other artery or vein can be suitably selected so long as sufficient amount of blood to carry out the desired dialysis/filtration operation can be obtained.

One might consider that the insertion of the needle-shaped pipe 40 for detecting blood pressure through the puncture needle 42 increases a resistance against blood current in the puncture needle 42. However, when a very thin needle having an outer diameter of about 25 gage is employed as the needle-shaped pipe 40 for detecting blood pressure, the existence of the needle-shaped pipe 40 for detecting blood pressure does not increase the resistance against blood current in the needle 42 and in the tube 44, because a puncture needle 42 one having an outer diameter of 15 to 17 gage is usually employed to obtain enough blood, and a tube 44 one having an inner diameter of about 6 mm is employed.

In the above-mentioned blood clarification apparatus, the value of blood pressure detected by the pressure transducer 34 through the needle-shaped pipe 40 for detecting blood pressure is input to the water-removal/supplementary-fluid-supply control device 32 and the value is compared with the reference value previously set by the setting device 36. Thus, conditions of the patient during the dialysis/filtration operation can be monitored automatically and continuously, and treatments suited to the conditions are carried out automatically and quickly.

A lower limit of blood pressure (for example, 70% of initial value of blood pressure) and allowable maximum decreasing rate of blood pressure (for example, 20 mmHg/min) are previously set by, for example, the setting device 36, and value of blood pressure input from the pressure transducer 34 is compared with the set value in the device 32. When the input value is out of the tolerance, suitable treatment is carried out; that is, an operation signal is transmitted to the dialyzate-supply/water-removal control device 24 and to the fluid carry pump 30 so that the operation of the device 24 is controlled to make the amount of the water removal substantially zero, and a predetermined amount of supplemetary fluid is supplied into the blood vessel at a constant rate (for example, an amount of about 100 ml and a rate of about 200 ml/min) by the pump 30.

Figure 3:
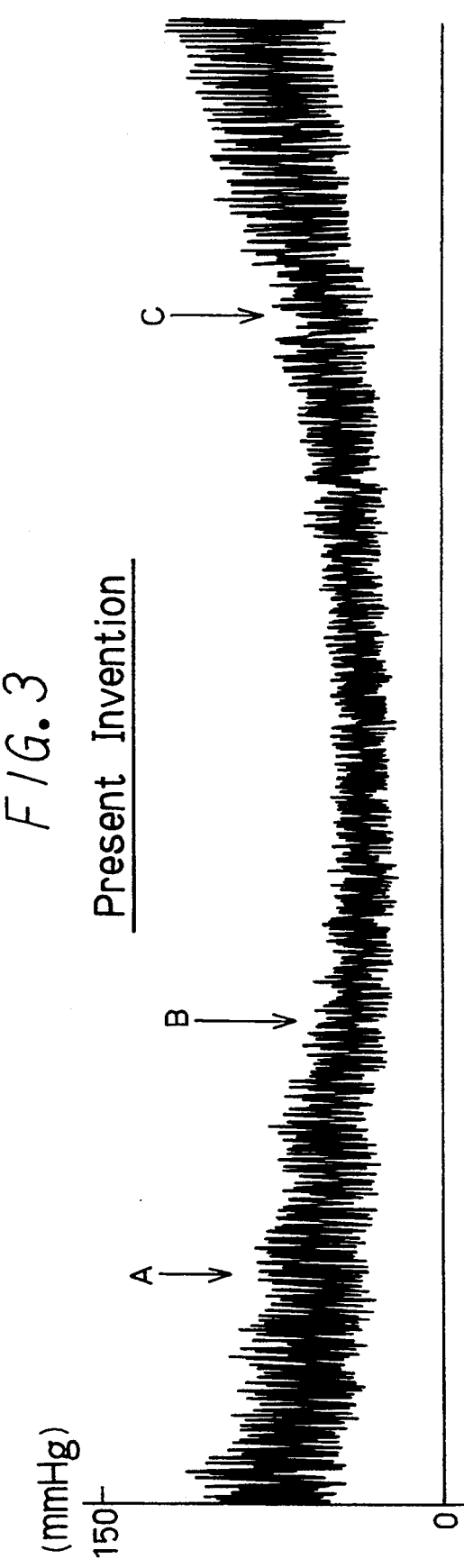
FIG. 3 shows two graphs wherein the upper graph indicates blood pressure continuously detected, with a needle-shaped pipe for detecting blood pressure placed inside a puncture needle, during actual dialysis operation using the blood clarification apparatus shown in FIGS. 1 and 2, and the lower graph indicates blood pressure detected with a normal needle punctured into an artery.
Figure 3:
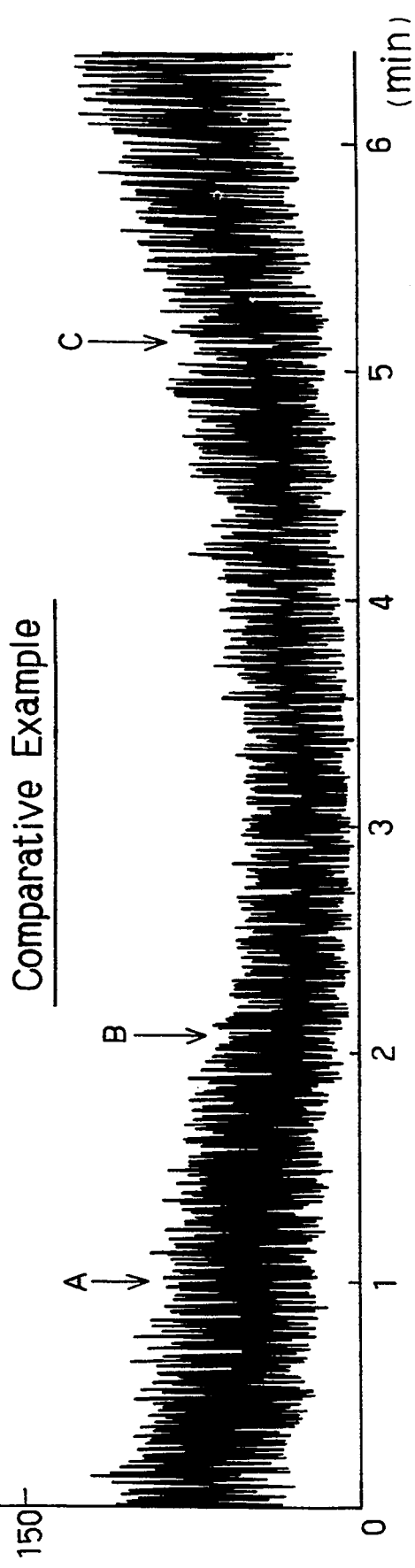
Figure 4:
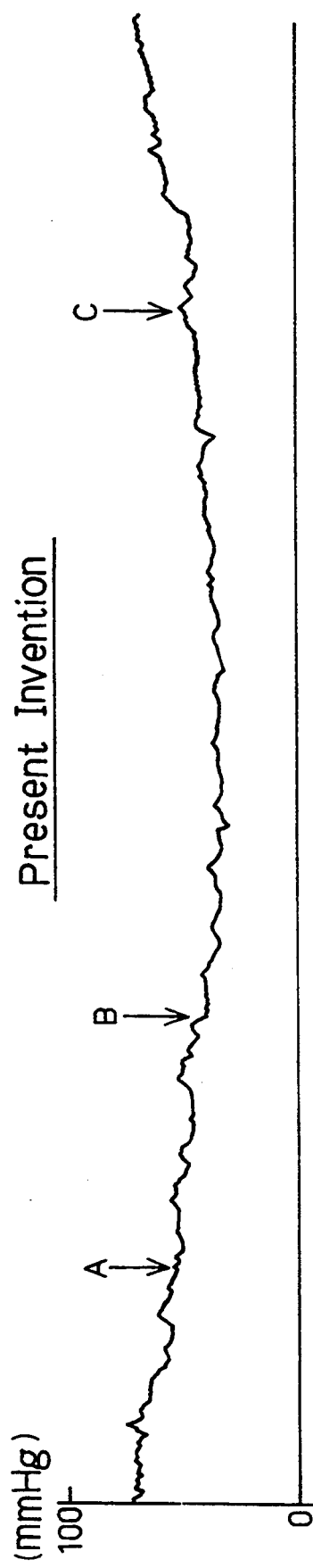
FIG. 4 shows two graphs indicating average value of blood pressure shown in FIG. 3 wherein the upper graph is concerned with blood pressure detected with the needle-shaped pipe for detecting blood pressure placed inside the puncture needle, and the lower graph is concerned with blood pressure detected with the normal needle punctured into the artery.
Figure 4:
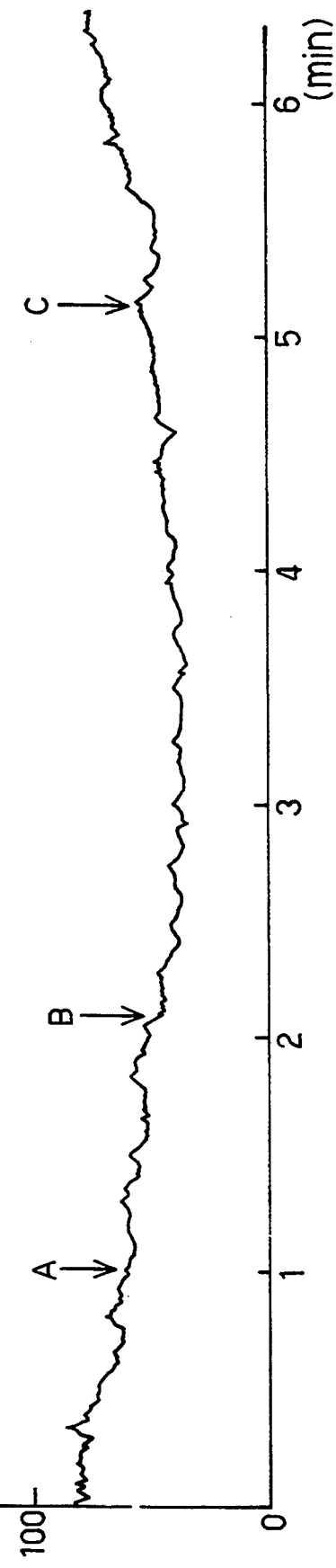

A dialysis operation was carried out with the blood clarification apparatus shown in FIGS. 1 and 2 with a fistula of an arm of a patient being installed with the puncture needle 42 and the needle-shaped pipe 40 for detecting blood pressure. The value of blood pressure continuously detected during the operation is partly shown in FIGS. 3 and 4. In FIG. 3, variation between maximum and minimum blood pressure is shown and in FIG. 4 the average value thereof calculated mathematically is shown. In both FIGS. 3 and 4, the upper graph indicates blood pressure measured by the needle-shaped pipe 40 for detecting blood pressure placed within the puncture needle 42. The dialysis operation was controlled depending on this variation of blood pressure. The lower graph indicates blood pressure (arterial pressure) measured by a usual needle for measuring blood pressure sticked into an artery of another arm of the patient for comparison. The upper and lower graphs are recognized to have the same correlation, whereby it is found that a blood pressure corresponding to an arterial pressure is exactly detected by the needle-shaped pipe 40 for detecting blood pressure placed within the puncture needle 42.

In this dialysis operation, the amount of blood current was set at 200 ml/min, and water removal was stopped when blood pressure detected was lowered to 70% (point A in FIG. 3) of an initial value (the value of the blood pressure at the beginning of the dialysis). When it was further lowered to 60% (point B in Figs.), 100 ml of supplementary fluid was supplied at a rate of 200 ml/min, and when it rose to 70% (point C in Figs.) again the water removal was started again. Thereby, the dialysis operation could be continued while effectively avoiding the dialysis hypotension.

Although an embodiment of the blood clarification apparatus of the present invention is explained in detail above, it should be noted that it is merely an embodiment and the present invention should not be limited to that embodiment. A dialysis device is employed as a blood clarification device in the above embodiment; however it is apparent that the present invention can be advantageously applied to a filtration device with which clarification of and water removal from blood is carried out by merely filtering action of semipermeable membrane without using dialyzate, and further to a dialysis/filtration device with which blood is clarified by dialyzing action and filtering action.

In the above embodiment, a rubber valve is employed as the insertion aperture 46 formed on the tube 44 serving as the blood supply passage 12 so that the needle-shaped pipe 40 for detecting blood pressure is easily inserted into the puncture needle 42 from outside. It is possible to employ, as the aperture, any kind of known materials and structures as occasion demands. As to the needle-shaped pipe 40 for detecting blood pressure, it is generally formed with metal such as stainless steel or with synthetic resin of good biocompatibility (a characteristic not showing adverse effect on blood), for example, polytetrafluoroethylene, silicone rubber or the like. In consideration of blood vessel damage, it is preferable to make the needle-detector 40 from synthetic resin. It should be understood that, in addition to the above embodiment, various changes, modifications and improvements can be applied based on the knowledge of a person skilled in the art as long as it does not depart from the subject matter of the present invention.

While the invention has been particularly shown and described in reference to preferred embodiments thereof, it will be understood by those skilled in the art that changes in form and details may be made therein without departing from the spirit and scope of the invention.

What is claimed is:

1. A blood clarification apparatus, comprising:
    means for taking blood out of a blood vessel of a patient, said means for taking blood including a puncture needle and a blood supply passage through which said blood flows;
    dialyzing and/or filtering means for receiving and clarifying said blood from said means for taking blood;
    blood carry passage means, operably coupled to said dialyzing and/or filtering means, for carrying blood back from said dialyzing and/or filtering means to said patient;
    dialyzate supply and removal control means, operably coupled to said dialyzing and/or filtering means, for controlling an introduction or removal of dialyzate and a flow rate and pressure thereof to or from said blood in said dialyzing and filtering means, said dialyzate supply and removal control means also controlling water removal by said dialyzing and/or filtering means;
    water-removal/supplementary-fluid-supply control means, operably coupled to said dialyzing and/or filtering means and to said dialyzate supply and removal control means, for controlling: (a) said dialyzate supply and removal control means, and (b) supply of supplementary fluid to said dialyzing and/or filtering means; and
    a blood pressure measuring means, operably coupled to said water-removal/supplementary-fluid-supply control means, for continuously measuring blood pressure of said patient, water removal rate and/or supplementary fluid supply rate being controlled based on readings of said blood pressure measuring means,
    wherein said blood pressure measuring means comprises:
    a pressure transducer, and
    a needle-shaped pipe for detecting a blood pressure, having a tip end portion which is placed to sufficiently project from a tip end portion of the puncture needle and is sticked into the blood vessel in an inverse direction relative to a blood current, from outside of the patient through an inner aperture of said puncture needle and is kept sufficiently deep inside the blood vessel, said needle-shaped pipe further having an inner aperture which is filled with a liquid solution so as to prevent blood from entering therein by which a blood pressure inside the blood vessel is transmitted to said liquid solution and further transmitted to said pressure transducer,
    said pressure transducer, operably coupled to said needle-shaped pipe for detecting a blood pressure, for continuously detecting said blood pressure within said blood vessel transmitted thereto through said needle-shaped pipe for detecting a blood pressure.

* * * * *

UNITED STATES PATENT AND TRADEMARK OFFICE
CERTIFICATE OF CORRECTION

PATENT NO. :   5,370,123
DATED      :   December 6, 1994
INVENTOR(S):   Toru SHINZATO It is certified that error appears in the above-identified patent and that said Letters Patent is hereby corrected as shown below:

On the title page, Item [30], "Apr. 4, 1991" should read -- Feb. 4, 1991--.

Signed and Sealed this

Eleventh Day of April, 1995

Attest:

BRUCE LEHMAN

Attesting Officer

Commissioner of Patents and Trademarks